United States Patent
Watkins et al.

[11] Patent Number: 6,013,039
[45] Date of Patent: Jan. 11, 2000

[54] PATELLA DISPLACEMENT TESTER

[75] Inventors: K. Richard Watkins; Donald C. Fithian, both of San Diego, Calif.

[73] Assignee: Medmetric Corporation, San Diego, Calif.

[21] Appl. No.: 09/025,352

[22] Filed: Feb. 18, 1998

[51] Int. Cl.[7] .................................................. A61B 5/103
[52] U.S. Cl. ........................ 600/595; 600/587; 33/512; 73/379.01
[58] Field of Search ................... 600/587, 595; 33/511, 512; 73/379.01

[56] References Cited

U.S. PATENT DOCUMENTS

| | | | |
|---|---|---|---|
| D. 352,111 | 11/1994 | Watkins | D24/140 |
| 563,468 | 7/1896 | Fergusson | 2/24 |
| 2,377,339 | 6/1945 | Greene | 2/24 |
| 3,214,501 | 10/1965 | Strauss | 264/49 |
| 3,463,147 | 8/1969 | Stubbs | 128/80 |
| 3,680,386 | 8/1972 | Cannon | 73/379 R |
| 4,084,584 | 4/1978 | Detty | 602/26 |
| 4,296,744 | 10/1981 | Palumbo | 128/80 C |
| 4,485,825 | 12/1984 | Domjan et al. | 600/587 |
| 4,501,266 | 2/1985 | McDaniel | 128/69 |
| 4,534,364 | 8/1985 | Lamoreux | 128/774 |
| 4,549,555 | 10/1985 | Fraser et al. | 128/782 |
| 4,583,554 | 4/1986 | Mittelman et al. | 128/774 |
| 4,583,555 | 4/1986 | Malcom et al. | 128/782 |
| 4,649,934 | 3/1987 | Fraser et al. | 128/782 |
| 4,799,497 | 1/1989 | Riley, II | 128/774 |
| 4,804,000 | 2/1989 | Lamb et al. | 600/587 |
| 4,822,365 | 4/1989 | Walker et al. | 623/18 |
| 4,911,177 | 3/1990 | Lamb et al. | 600/595 |
| 4,913,163 | 4/1990 | Roger et al. | 600/595 |
| 4,969,471 | 11/1990 | Daniel et al. | 128/774 |
| 4,989,337 | 2/1991 | Mason et al. | 600/587 |
| 5,148,606 | 9/1992 | Mason et al. | 600/587 |
| 5,156,163 | 10/1992 | Watkins et al. | 128/782 |
| 5,267,951 | 12/1993 | Ishii | 602/26 |
| 5,333,604 | 8/1994 | Green et al. | 601/33 |
| 5,556,374 | 9/1996 | Grace et al. | 602/26 |
| 5,673,708 | 10/1997 | Athanasiou et al. | 600/587 |

*Primary Examiner*—Cary O'Connor
*Assistant Examiner*—Charles Marmor, II
*Attorney, Agent, or Firm*—Nydegger & Associates

[57] ABSTRACT

A device for evaluating the patellafemoral joint is provided herein. The device measures movement of the patella in response to a lateral test force applied against the patella by a displacer, when the leg is supported in a flexed, relaxed position. The testing device includes a monitor which measures displacement of the patella. The monitor includes a monitor base that is secured to the leg of a patient and a contact arm which moves with the patella. The magnitude of the test force can be correlated with the degree of leg flexion and displacement of the patella to indicate the health and condition of the tissues in the knee which resist dislocation and movement of the patella.

21 Claims, 6 Drawing Sheets

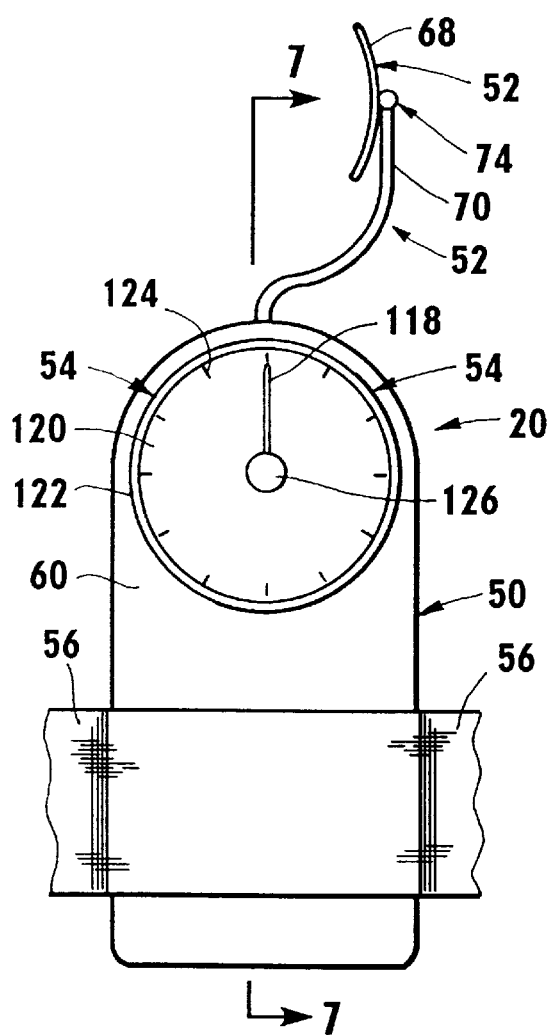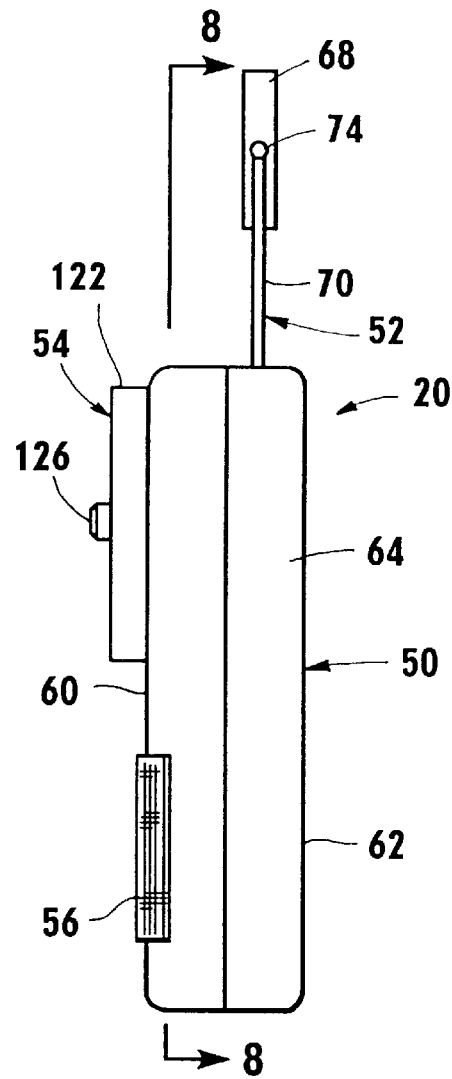
Fig. 4　　　　Fig. 5
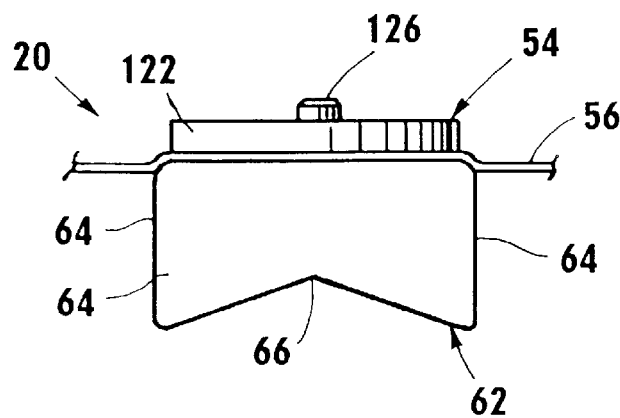
Fig. 6

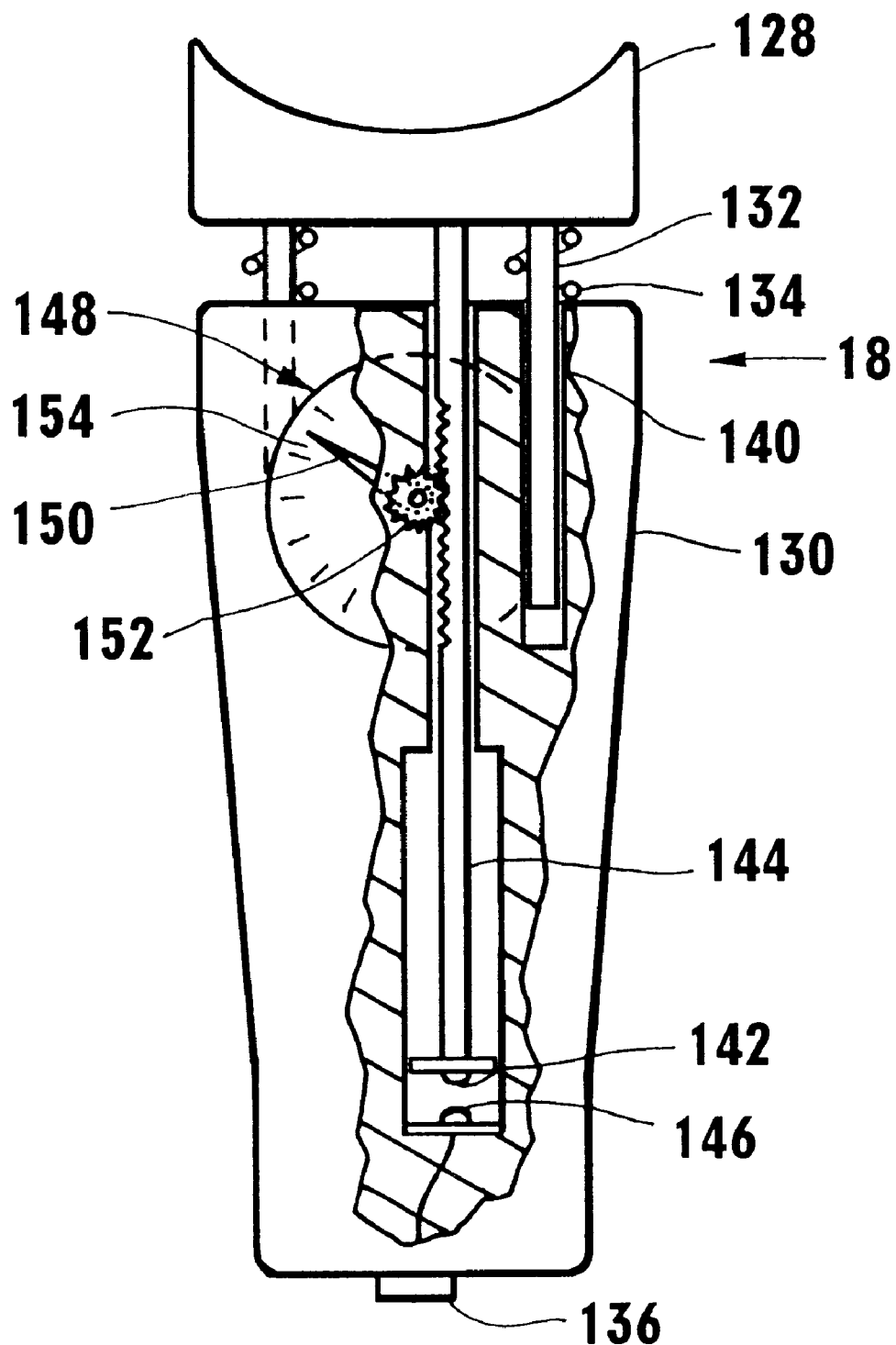

PATELLA DISPLACEMENT TESTER

FIELD OF THE INVENTION

The present invention is directed to medical devices useful for evaluating the condition of a human joint. More specifically, the present invention relates to a device for testing the stability of the patellofemoral joint.

BACKGROUND

Traumatic injuries can be very painful and debilitating. In many cases, an early diagnosis of the damage significantly helps in prescribing proper treatment for alleviating the pain and minimizing the injury. Unlike some other types of traumatic injuries, injuries to joints frequently result in impaired or abnormal movement between the connected bone structure. For example, the extent of the damage or injury to a knee joint can be evaluated by observing the knee's ability to move the lower leg, i.e., the tibia, with respect to the upper leg, i.e., the femur. Additional information regarding the condition of the knee joint can be obtained by measuring the amount of displacement of the patella.

The patella or kneecap is a flat, triangular shaped bone which is positioned at an anterior portion of the knee joint which connects the femur to the tibia. The patella is attached and maintained in position at the anterior portion of the knee joint with ligaments and muscles. The primary purposes of the patella is to protect the front of the knee joint and increase the leverage of the quadriceps extensors. A main medical concern relating to the patella involves the tearing of the ligaments which retain the patella in position.

Typically, doctors will move the patella with their hand or X-ray the knee joint to evaluate the extent of the injury to the patella and/or the ligaments connecting the patella. However, doctors are not always able to quickly and accurately determine the extent of damage to the ligaments with an X-ray. Further, movement of the patella by hand is inaccurate and unreliable.

In light of the above, it is an object of the present invention to provide a device which can accurately determine whether the ligaments which align the patella have been damaged. Further, it is an object of the present invention to provide a device can be used to quickly and accurately evaluate the extent of injury to the knee joint of a patient. Still another object of the present invention to provide a device which is relatively easy to use, is relatively safe to use and relatively inexpensive.

SUMMARY

The present invention is directed to a testing device for measuring the displacement of a patella in a leg of a patient which satisfies these objectives. The testing device accurately measures the displacement of the patella which results from an application of a test force to the patella. Thus, the testing device can be used by a physician to quickly and accurately diagnose the extent of damage to the ligaments of a knee joint.

The testing device includes a monitor having a monitor base which secures to the leg of the patient and a contact arm which moves with the patella. Typically, the monitor base is attached to the leg below the patella. The contact arm extends away from the monitor base and includes a contact surface which contacts the leg proximate the patella and moves with the patella. Typically, the contact arm includes a curved contact surface which is shaped to contact the leg.

The monitor includes a display which displays the displacement of the patella upon application of the test force. Preferably, the display can be "zeroed" or calibrated prior to testing. The display can be "zeroed" by positioning the contact surface against the leg and moving the display to read zero. This allows the physician to easily determine the displacement of the patella.

As provided herein, the monitor can include a transfer assembly which transfers motion of the contact arm into motion of the display. Preferably, the transfer assembly also amplifies the motion of the contact arm relative to the monitor base into rotational movement of the display. This allows for an easier reading of the display even upon minimal displacement of the patella.

The testing device can also include a displacer for accurately applying the test force to the patella. The accurate application of the test force facilitates accurate evaluation of the condition of the knee joint. For example, the magnitude of the test force can be correlated with the degree of leg flexion and the displacement of the patella to evaluate the health and condition of the tissues in the knee which resist dislocation or movement of the patella. Typically, a substantially lateral test force, relative to the knee joint, is applied to the patella and the monitor measures substantially lateral movement of the patella.

As provided herein, the displacer can include a pressure pad, a handle and a signaler. The pressure pad is used for contacting the leg proximate the patella and transferring the test force from the displacer to the patella. Alternately, the pressure pad can be designed for contacting the contact arm opposite the curved contact surface of the monitor. In this embodiment, the test force is transferred through the contact arm to the patella. The handle is adapted for gripping by a human. This allows the present testing device to be used in remote locations without the use of external power.

The signaler signals when the desired test force is applied to leg. The amount of test force can be varied according to the preference of the physician. Typically, the signaler is set to signal when a test force is applied to the pressure pad of between approximately two to twenty pounds (2–20 lbs.), and more preferably, between approximately five to ten pounds (5–10 lbs.)

The present invention is also directed to a method for measuring the movement of a patella in a leg of a patient. The method includes the steps of applying a substantially lateral test force to the patella, and detecting lateral displacement of the patella with a monitor having a monitor base which is attached to the leg of the patient.

Importantly, the unique design of the testing device allows for the simple and accurate measurement of the displacement of the patella in the leg of the patient. This allows a physician to quickly evaluate the health and condition of the tissues of the knee which resist dislocation and movement of the patella. Further, the evaluation of the knee joint can be accomplished without exposing the patient to radiation.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 4 is a top plan view of a monitor having features of the present invention;

FIG. 5 is a side plan view of the monitor of FIG. 4;

FIG. 6 is an end plan view of the monitor of FIG. 4;

FIG. 9 is a top plan view, in partial cut-away, of a displacer having features of the present invention.

DESCRIPTION

Figure 1A:
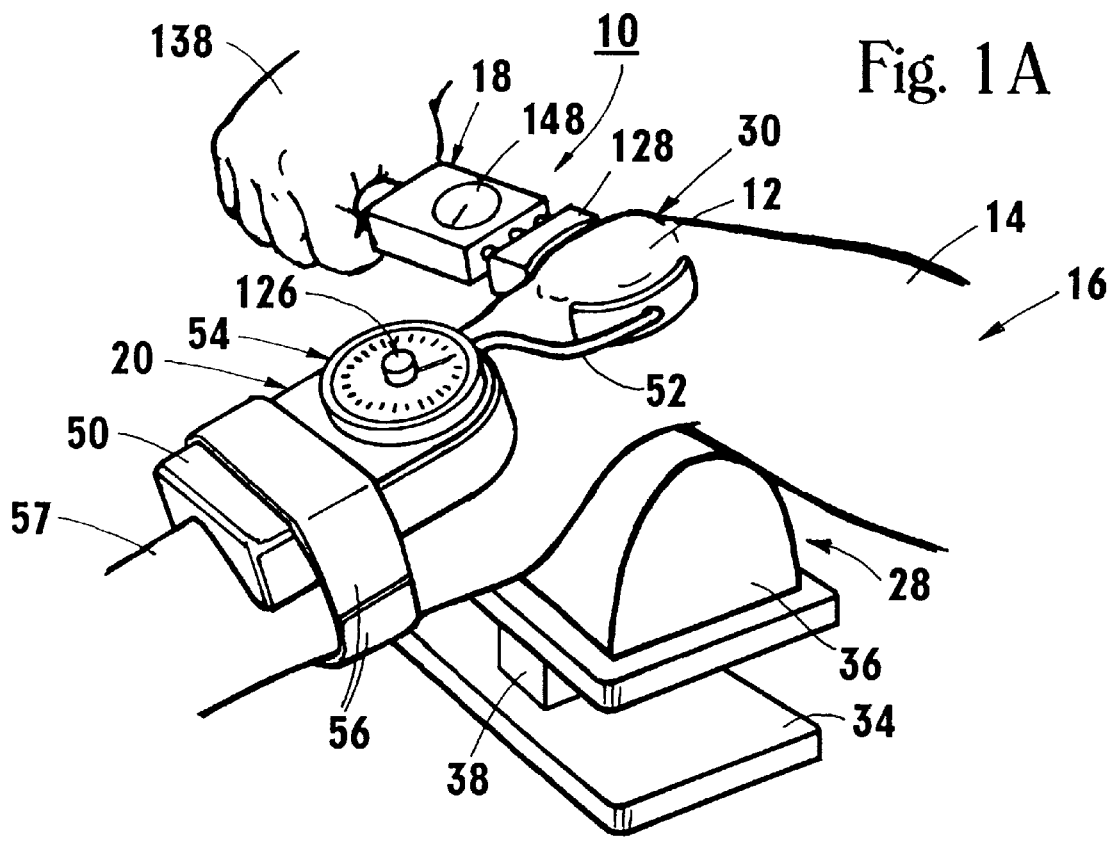
FIG. 1A is a perspective view of a testing device having features of the present invention, and a leg of a patient.
Figure 1B:
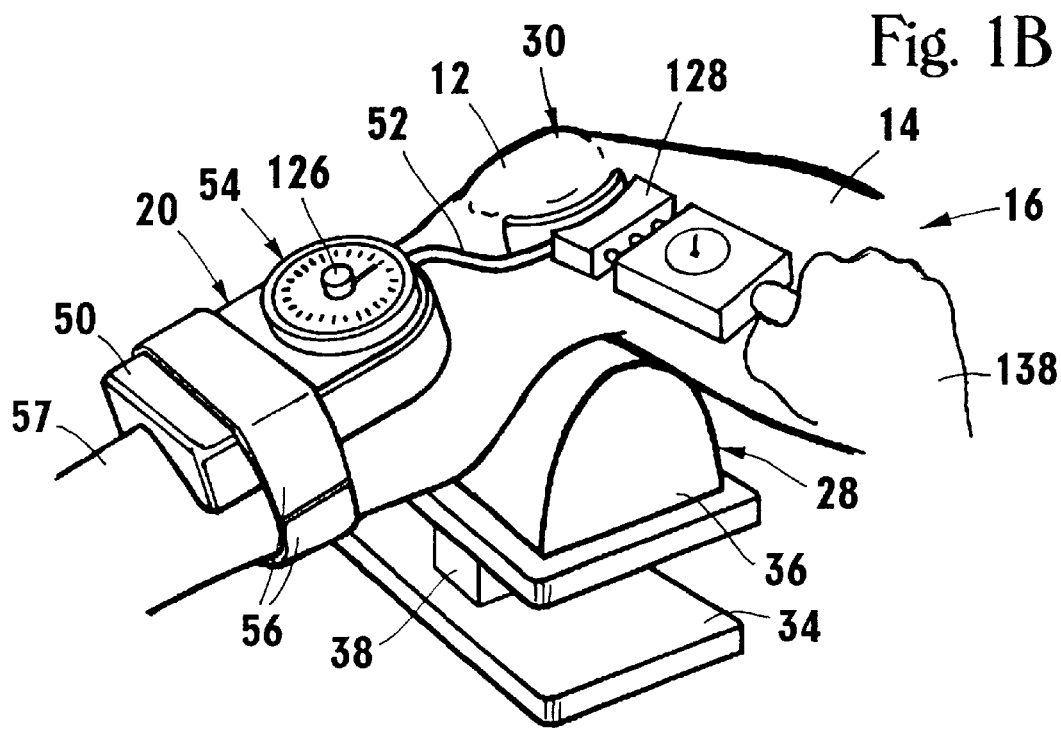
FIG. 1B is a second perspective of a testing device and a leg of a patient.

Referring initially to FIGS. 1A and 1B, a testing device 10 for measuring the movement of a patella 12 (shown in phantom in FIG. 1) in a leg 14 of a patient 16, according to the present invention includes a displacer 18 and a monitor 20. The displacer 18 is used to apply a test force to the patella 12, while the monitor 20 measures the amount of displacement of the patella 12. Based upon the amount of displacement of the patella 12, a physician (not shown) can quickly and accurately evaluate the condition of the knee and/or the ligaments (not shown) which support the patella 12.

Importantly, the testing device 10 is relatively simple and easy to use. Further, the testing device 10 can be used without external power. Thus, the testing device 10 can be used in remote locations to evaluate the condition of the ligaments which support the patella 12 and the patient 16 is not subjected to potentially harmful radiation.

Figure 2:
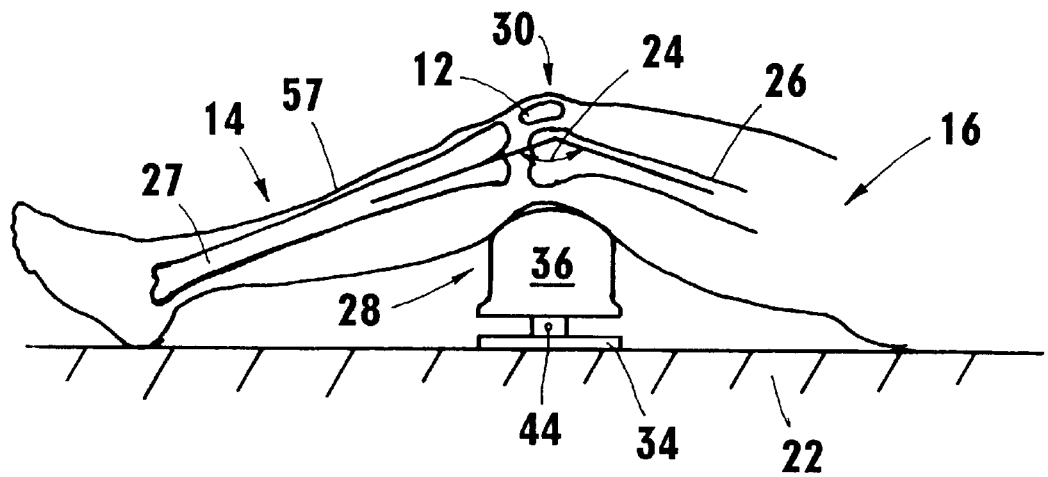
FIG. 2 is a side plan view of the leg of the patient and a leg support having features of the present invention.

Referring to FIG. 2, the displacement of the patella 12 is typically evaluated while the patient 16 is lying on a relatively fixed surface 22 such as a physician table. While on the fixed surface 22, the leg 14 of the patient 16 is slightly bent so that the ligaments which support the patella 12 are relaxed. Typically, the leg 14 is bent so that a flexion angle 24 formed between the femur 26 and the tibia 27 at the knee joint 30 is between approximately one hundred and thirty degrees to one hundred and seventy degrees (130°–170°), and more preferably between approximately one hundred and forty degrees to one hundred and fifty degrees (140°–150°).

To facilitate bending of the leg 14, a leg support 28 can be positioned between the fixed surface 22 and the leg 14 substantially opposite the patella 12. Preferably, the height of the leg support 28 is adjustable so that the flexion angle 24 can be adjusted according to the requirements of the patient 16 and the preferences of the physician.

Figure 3:
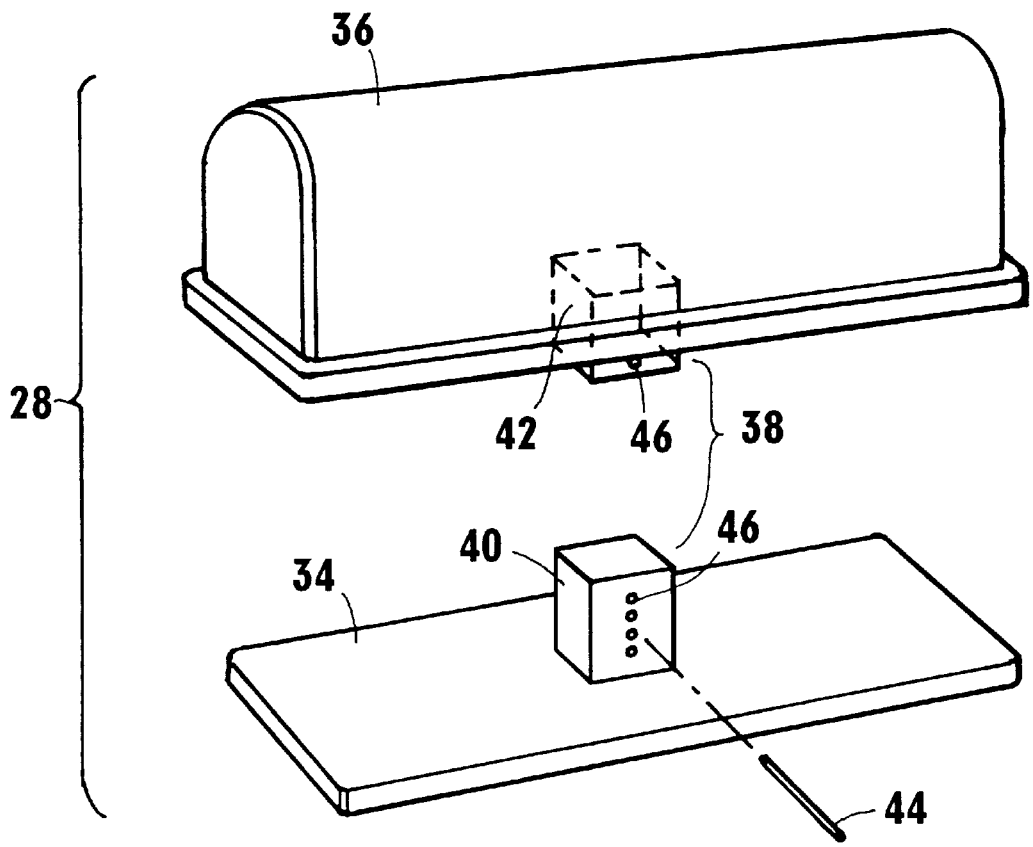
FIG. 3 is an exploded perspective view of a leg support having features of the present invention.

The leg support 28 can be implemented in a number of alternate ways. For example, as can best be seen from FIG. 3, the leg support 28 can include a support base 34, a support contact 36, and a support adjuster 38. The support base 34 is substantially flat, rectangular, and designed to be stable when positioned on the fixed surface 22. The support contact 36 contacts the leg 14 and can have a semi-circular cross-section. The support contact 36 can be padded for the comfort and safety of the patient 16.

The support adjuster 38 adjusts the distance or space between the support base 34 and the support contact 36. In the embodiment shown in FIG. 3, the support adjuster 38 includes a rectangular projection 40 which extends away from the support base 34 and a rectangular opening 42 in the support contact 36 which is sized and shaped to receive the projection 40. In this embodiment, a support pin 44 can be selectively positioned within support apertures 46 in the support base 34 and support contact 36 to adjust the height of the leg support 28. Alternately, for example, the support adjuster 38 can include an externally threaded rod (not shown) which is mounted to the support base 34 and an internally threaded member (not shown) which is mounted to and rotates relative to the support contact 36. In this embodiment, the space between the support base 34 and the support contact 36 can be modified by rotating the internally threaded member. Those skilled in the art will recognize other ways to design an adjustable leg support 28 with the teachings of the present disclosure.

The monitor 20 accurately measures and detects the displacement of the patella 12 which results from the application of the test force upon the patella 12. This allows the physician to quickly evaluate the condition of the ligaments which retain the patella 12. Referring back to FIGS. 1A and 1B, the monitor 20 is typically used to measure substantially lateral movement of the patella 12 relative to the knee joint 30.

Figure 7:
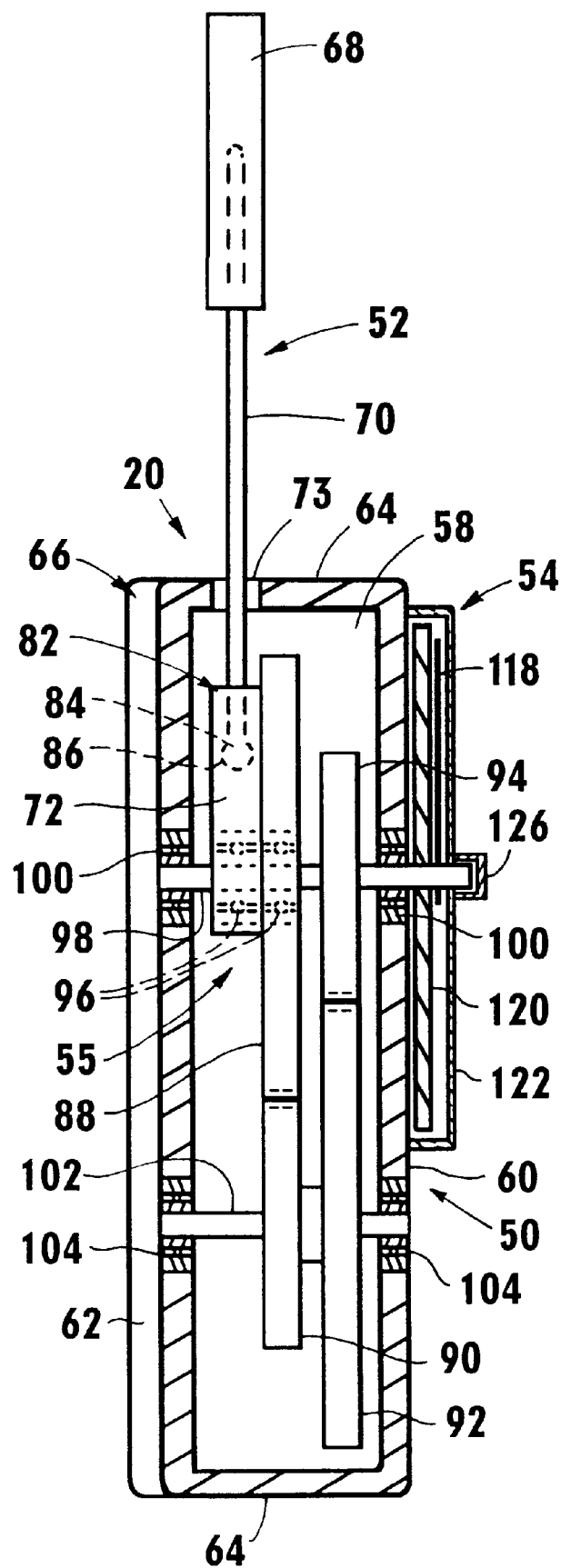
FIG. 7 is a cut-away view taken on line 7—7 of FIG. 4.
Figure 8:
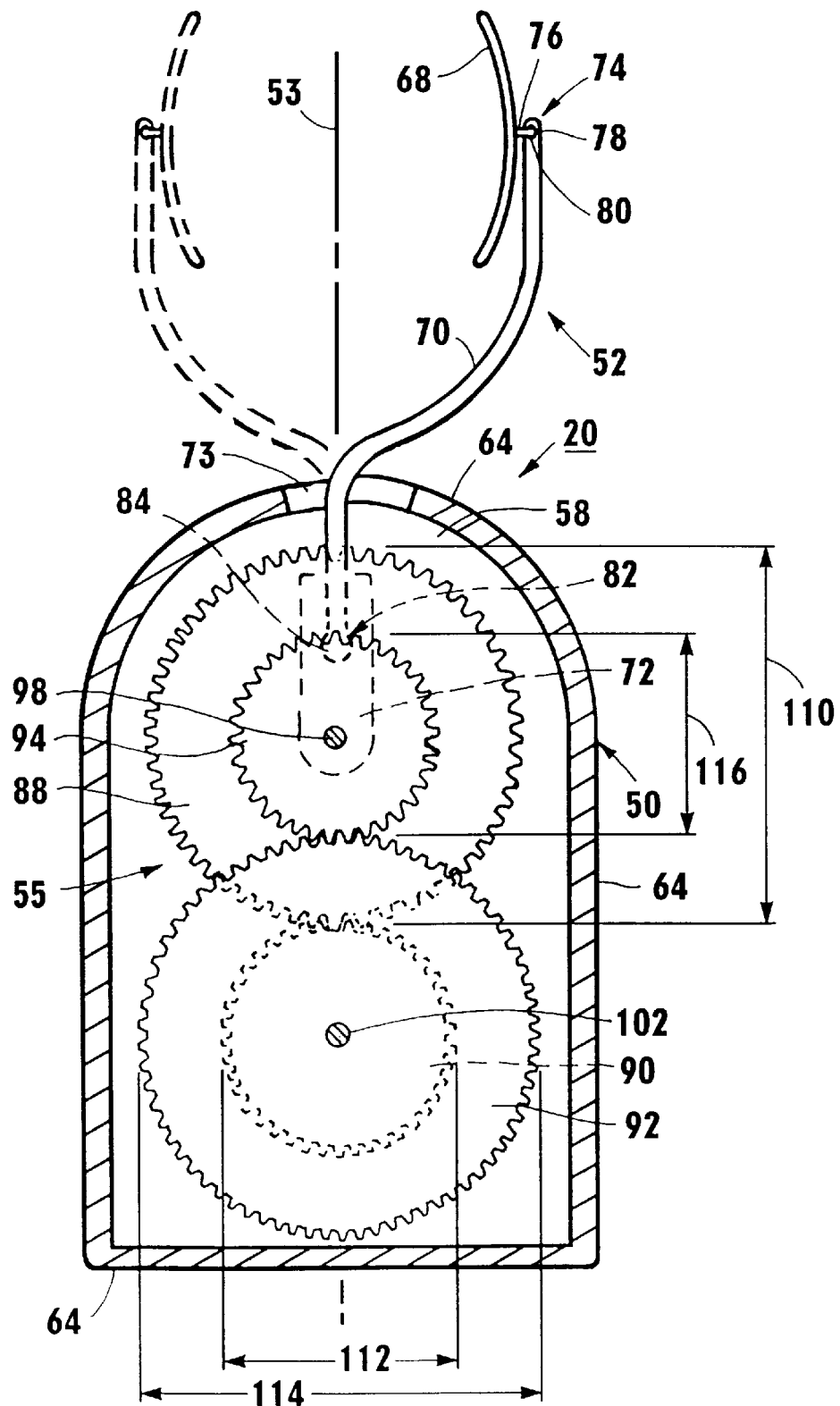
FIG. 8 is a cut-away view taken on line 8—8 of FIG. 5.

As can probably best be seen with reference to FIGS. 4, 5, 7, and 8, the monitor 20 includes a monitor base 50, a contact arm 52, a display 54, and a transfer assembly 55 (shown in FIGS. 7 and 8). The monitor base 50 is adapted to be selectively attached to the leg 14. The monitor base 50 can be attached to the leg 14 in a number of alternate ways. For example, in the embodiment shown in the FIG. 1, the monitor base 50 includes a strap 56 which extends away from the monitor base 50 and wraps around the leg 14. The ends of the strap 56 can be secured together with hook and loop type fasteners or some other type of fastener. Alternately, those skilled in the art will recognize other ways to secure the monitor base 50 to the leg 14. Importantly, the monitor base 50 should be securely attached to the leg 14 to ensure accurate measurements with the monitor 20.

As shown in FIG. 1, the monitor 20 can be attached to the leg 14 below the patella 12 and proximate a shin 57 of the patient 16. Alternately, for example, the monitor 20 can secured lower on the leg 14 than shown in FIG. 1 or possibly above the patella 12.

Referring to FIGS. 7 and 8, the monitor base 50 has a longitudinal axis 53 and includes an inner cavity 58 which encloses the transfer assembly 55. The inner cavity 58 is defined by a top surface 60 which supports the display 54, a bottom surface 62 and four, spaced apart, side surfaces 64. As can best be seen in FIG. 6, the bottom surface 62 is adapted for contacting the leg 14 and can include a longitudinally extending groove 66 to fit the leg 14.

The contact arm 52 extends away from the monitor base 50 and moves with the patella 12. The contact arm 52 includes a contact surface 68, an extension arm 70, and a contact mount 72. The contact surface 68 is shaped for contacting the leg 14 proximate the patella 12 and moving with the patella 12. In the embodiment shown in the Figures, the contact surface 68 is curved to fit the contour of the side of the patella 12. The contact surface 68 can be padded for comfort to the patient 16.

The extension arm 70 extends between the contact surface 68 and the contact mount 72. In the embodiment shown in FIGS. 7 and 8, the extension arm 70 extends through an arm aperture 73 in the monitor base 50. In this embodiment, the arm aperture 73 is sufficiently large to allow for movement of the extension arm 70 relative to the monitor base 50. As can best be seen with reference to FIGS. 1, 4, and 8, the extension arm 70 can be a rod which is curved so that when the monitor 50 is attached to the leg 14, the contact surface 68 contacts the leg 14 near one of the sides of the patella 12. Preferably, the contact surface 68 is attached to the extension arm 70 with a contact swivel connector 74 so that the contact surface 68 can tilt to fit against the patella 12. As can best be seen in FIG. 8, the contact swivel connector 74 can include a pin 76 having a substantially spherical end 78 which extends away from the contact surface 68 and fits into a substantially spherical aperture 80 in the extension arm 70. Those skilled in the art will recognize other ways to design the contact swivel connector 74.

Referring to FIGS. 7 and 8, the contact mount 72 attaches the extension arm 70 to the transfer assembly 55. Preferably, the contact mount 72 and/or the extension arm 70 includes a mount swivel connector 82 so that the extension arm 70 can be rotated relative to the monitor base 50. This allows the extension arm 70 and the contact surface 68 to be rotated so that the contact surface 68 can be placed against either side of the patella 12 to allow the device 10 to be rotated to measure displacement from either side of the patella 12 (not shown in FIG. 8) as shown in phantom in FIG. 8. In the embodiment shown in FIGS. 7 and 8, the mount swivel connector 82 can include a substantially spherical ball 84 secured to the end of the extension arm 70. The spherical ball 84 and a portion of the extension arm 70 fit into a ball receiver 86 having a spherical shaped opening in the contact mount 72. Those skilled in the art will recognize other ways to design the mount swivel connector 82.

The contact mount 72 is secured to the transfer assembly 55 which transfers motion of the contact arm 52 into motion of the display 54. Preferably, the transfer assembly 55 increases the magnitude of the motion transferred to the display 54. Stated another way, preferably, because of the transfer assembly 55, a relatively slight movement of the contact arm 52 will result in a more significant movement of the display 54. This allows for easier reading of the display 54. A suitable transfer assembly 55 can result in an increase of magnitude of between approximately 2:1 to 10:1.

In the embodiment shown in FIGS. 7 and 8, the transfer assembly 55 includes an input component 88, a first transfer component 90, a second transfer component 92, and an output component 94. In this embodiment, the contact mount 72 is secured to the input component 88 so that movement of the extension arm 70 results in rotation of the input component 88. Referring to FIG. 7, the contact mount 72 and the input component 88 are mounted with a pair of shaft bearings 96 to an input shaft 98 while the output component 94 is fixedly secured to the input shaft 98. Further, the input shaft 98 is attached with a pair of base bearings 100 to the top surface 60 and the bottom surface 62 of the monitor base 50. This allows the contact mount 72 and the input component 88 to rotate relative to the input shaft 98 and output component 94. Further this allows the input component 88 and the output component 94 to rotate relative to the monitor base 50.

Somewhat similarly, the first transfer component 90 and the second transfer component 92 are fixedly secured to a transfer shaft 102. The transfer shaft 102 is attached with a second pair of base bearings 104 to the top surface 60 and the bottom surface 62 of the monitor base 50. This allows the first transfer component 90 and the second transfer component 92 to rotate relative to the monitor base 50. Further, the input component 88 is connected to the first transfer component 90 and the second transfer component 92 is connected to the output component 94. This allows rotation of the input component 88 to result in rotation of the first transfer component 90 and rotation of the second transfer component 92 to result in rotation of the output component 94.

As provided above, the transfer assembly 55 preferably increases the magnitude of the motion transferred to the display 54. This can be accomplished by the proper sizing of the components 88, 90, 92, 94 of the transfer assembly 55. For example, as best can be seen in FIG. 8, each of the components 88, 90, 92, 94 can be a gear. In this embodiment, the teeth of the input component 88 meshes with the teeth of the first transfer component 90 while the teeth of the second transfer component mesh with the teeth of the output component 94. Further, in this embodiment, the input component 88 has an input component diameter 110 which is larger than a first transfer component diameter 112 of the first transfer component 90, and the second transfer component 92 has a second transfer component diameter 114 which is larger than the first transfer component diameter 112 and a output component diameter 116 of the output component 94. Those skilled in the art should recognize other ways to design the transfer assembly 55 from the teachings provided herein. For example, a first chain (not shown) could be used to connect the input component 88 to the first transfer component 90 and a second chain (not shown) could be used to connect the second transfer component 92 to the output component 94. Alternately, each of the components 88, 90, 92, 94 can be shaped similar to a pulley and belts (not shown) could be used to connect the appropriate components.

The display 54 displays the movement of the patella 12 based upon movement of the contact arm 52. The display 54 can be implemented in a number of alternate ways. For example, in the embodiment shown in the figures, the display 54 includes a needle 118, a marked screen 120 and a display cover 122 which are positioned proximate to the top surface of the monitor base 50. As can probably best be seen from FIG. 7, the needle 118 is attached to and rotates with the input shaft 98. The marked screen 120 is positioned between the needle 118 and the top surface 60 and includes a plurality of equally spaced apart marks 124 (shown in FIG. 4) to measure movement. The distance between the marks 124 can be varied. Further, the marks 124 can be numbered (not shown). As provided herein, movement of the patella 12 results in the rotation of the input shaft 98 and the needle 118 relative to the marked screen 120. Therefore, the physician is able to determine movement of the patella 12 which results from application of the test force based upon movement of the needle 118 relative to the marked screen 120.

Preferably, the display 54 can be "zeroed" or calibrated prior to testing. The display 54 can be "zeroed" by positioning the contact surface 68 against the leg 14 and rotating the marked screen 120 relative to the needle 118 to read zero. This allows the physician to easily determine the displacement of the patella 12 upon application of the test force.

In the embodiment shown in the Figures, the display cover 122 covers the needle 118 and the marked screen 120 and is fixedly secured to the marked screen 120. Preferably, the display cover 122 can be rotated relative to the monitor base 50 and the needle 118 by rotation of a cover handle 126. This allows the physician to easily rotate the display cover 122 and the marked screen 120 with the cover handle 126 relative to the needle 118 to zero the display 54.

The displacer 18 is used to accurately apply the test force to the leg 14 proximate the patella 12 so that the resulting movement of the patella 12 can be evaluated. The amount of the test force can be varied according to the patient 16 and the preferences of the physician. For example, it is believed that a test force of between approximately two and twenty pounds (2–20 lbs.) force and more preferably between approximately three and ten pounds (3–10 lbs.) force can be used with the present invention. However, it should be recognized that too large of a test force can damage the patella 12 and/or the ligaments which support the patella 12.

The displacer 18 can be implemented in a number of alternate ways. In the embodiment shown in FIG. 9, the displacer 18 includes a pressure surface 128, a displacer body 130, a pair of guide shafts 132, a pair of resilient connectors 134, and a signaler 136. In this embodiment, the test force is applied by the physician gripping the displacer body 130 which is tubular and shaped to be retained by a human hand 138 (shown in FIG. 1). Alternately, for example, the displacer body 130 can be moved by a mechanical or electrical device (not shown) to apply the test force.

The pressure surface 128 is adapted for contacting the leg 14 proximate the patella 12 and applying the test force to the patella 12. In the embodiment shown in FIG. 1A, the test force is applied to the patella 12 substantially opposite from the contact surface 68. Thus, for the embodiment shown in FIG. 1A, the pressure surface 128 is preferably, slightly concave and sized and shaped to conform to the shape of the leg 14 by the patella 12. A pad (not shown) which conforms to the irregularities of the leg 14 by the patella 12 can also be attached to the pressure surface 128. Alternately, for the embodiment shown in FIG. 1B, the test force is applied through the contact arm 52 of the monitor 20. In this embodiment, the pressure surface 128 is adapted for contacting the contact surface 68.

The pressure surface 128 is attached to the displacer body 130 with the guide shafts 132 and the resilient connectors 134. As shown in FIG. 9, the guide shafts 132 can slide relative to the displacer body 130 within shaft apertures 140 in the displacer body 130 or a linear bearing. Further, in the embodiment in FIG. 9, the resilient connectors 134 are each positioned over one of the guide shafts 132, between the pressure surface 128 and the displacer body 130. The resilient connectors 134 minimize impulse shock to the patella 12 upon the application of the test force to the patella 12. In this embodiment in FIG. 9, each resilient connector 134 is a spring having a substantially constant spring constant. Alternately, for example, each resilient connector 134 can be an elastic material which is compressed (not shown).

The signaler 136 signals when approximately the desired test force is applied to the patella 12. This allows for the accurate application of the test force to the patella 12 and prevents the application of excessive force to the patella 12. The signaler 136 can be implemented in a number of alternate ways. For example, as shown in FIG. 9, the signaler 136 can be a light at the end of the displacer body 130 or an audio alarm which signifies when the desired test force is being applied to the leg 14.

As shown in FIG. 9, the signaler 136 can include a first contact 142 which is attached to a display shaft 144 and a second contact 146 which is secured to the displacer body 130. The display shaft 144 is attached to and moves with the pressure surface 128. The contacts 142, 146 are initially spaced apart prior to application of a test force to the patella 12. The amount of space between the contacts 142, 146 can vary according to the design of the resilient connectors 134. The contacts 142, 146 move together as force is applied to the patella 12. The displacer 18 is designed so that the two contacts 142, 146 engage proximate when the test force is applied to the leg 14 to close a circuit which sets off the signaler 136 to notify the physician that the test force is being applied to the patella 12.

Further, the displacer 18 can include a displacer gauge 148 providing a visual display of the amount of force being applied to the patella 12. In the embodiment shown in FIG. 9, the displacer gauge 148 includes a displacer needle 150 which is rotated by a displacer gear 152 which rotates upon movement of the display shaft 144. The displacer gauge 148 can also include a displacer screen 154 with spaced apart marks which represent the amount of force being applied to the patella 12.

OPERATION

The operation of the present testing device 10 can best be understood with initial reference to FIG. 1 which shows the leg 14 of a patient 16 slightly bent with the leg support 24 under the knee joint 30. The height of the leg support 24 can be adjusted to change the amount of bend of the leg 14 of the patient 16 to suit the needs of the physician. With the leg 14 in the bent position, the monitor 20 is securely attached to the leg 14 using the strap 56, with the contact surface 68 positioned against one of the sides of the patella 12. With the contact surface 68 proximate the side of the patella 12, the display 54 is zeroed by rotating the marked screen 120.

Next, the desired lateral test force is applied to the patella 12 with the displacer 18. Importantly, the signaler 136 signals when the desired test force is applied by the displacer 18 to prevent damage to the patella 12 from applying too much force. Upon the application of the test force, the patella 12 will move substantially laterally. The amount of movement will depend upon the condition of the ligaments which tend to maintain the patella 12 in position and the amount of test force. The movement of the patella 12 is accompanied by the movement of the contact arm 52 relative to the monitor base 50. Movement of the contact arm 52 results in movement of the contact mount 72 which is secured to the input component 88. Movement of the input component 88 results in rotation of the first transfer component 90 and the second transfer component 92 which is attached to the first transfer component 90. Rotation of the second transfer component 92 results in rotation of the output component 94, the input shaft 98, and the needle 118 relative to the marked screen 120. Based upon the position of the needle 118 relative to the marked screen 120, the physician is able to determine the relative movement of the patella 12.

The magnitude of the applied the force can be correlated with the value of the flexion angle 24 and the displacement of the patella 12 as measured by the monitor 20. From this information, the health and condition of the tissues in the knee which resist dislocation of the patellofemoral joint and promote alignment of the patella 12 within the joint can be evaluated.

Although the displacer 18 is shown in FIG. 1A as applying a test force to the outer portion of the leg 14, the test force can also be applied to the inner portion of the leg 14. Further, when the test force is applied to the patella 12, the test force is actually applied to the leg 14 through skin to the patella 12.

While the particular testing device 10 as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A testing device for measuring the displacement of a patella in a leg of a patient which results from an application of a substantially lateral test force to the patella, the testing device comprising:

a monitor adapted for measuring substantially lateral displacement of the patella upon application of the test force to the patella, the monitor including (i) a monitor base, (ii) a strap which is adapted to substantially encircle the leg and secure the monitor base to the leg of the patient, and (iii) a contact arm which connects to the monitor base and is adapted to move substantially laterally with the patella.

2. The testing device of claim 1 wherein the monitor base is adapted for selective attachment to the leg below the patella.

3. The testing device of claim 1 wherein the contact arm extends away from the monitor base and includes a contact surface which is adapted for contacting the leg proximate the patella and moving with the patella.

4. The testing device of claim 1 wherein the monitor includes a display which displays the measured displacement of the patella.

5. The testing device of claim 4 wherein the monitor includes a transfer assembly which transfers motion of the contact arm into motion of the display.

6. The testing device of claim 5 wherein the transfer assembly transfers motion of the contact arm relative to the monitor base into rotational motion of the display.

7. The testing device of claim 1 comprising a displacer for applying the test force to the patella.

8. The testing device of claim 7 wherein the displacer includes a pressure surface which is adapted for applying the test force to the patella.

9. The testing device of claim 7 wherein the displacer includes a handle which is adapted for gripping by a human.

10. The testing device of claim 7 wherein the displacer includes a signaler which signals when the test force is applied.

11. A testing device for measuring the displacement of a patella in a leg of a patient, the testing device comprising:

a displacer adapted for applying a test force to the patella, the displacer including: (i) a pressure surface which is adapted for applying the test force, (ii) a handle which is adapted for gripping, and (iii) a signaler which signals when the test force is applied to the pressure surface; and a monitor adapted for detecting displacement of the patella, the monitor including: (i) a monitor base, (ii) a strap which substantially encircles the leg and attaches the monitor base to the leg, below the patella, (iii) a contact arm which extends away from the monitor base, the contact arm including a contact surface which is adapted for moving with the patella, and (iv) a display which displays the displacement of the patella.

12. The testing device of claim 11 wherein the displacer includes a displacer connector which connects the pressure surface to the handle.

13. The testing device of claim 11 wherein the displacer connector includes a spring.

14. The testing device of claim 11 wherein the signaler signals when a test force is applied to the pressure surface of between approximately 2 to 20 pounds.

15. The testing device of claim 11 wherein the signaler signals when a test force is applied to the pressure surface of between approximately 5 to 10 pounds.

16. The testing device of claim 11 wherein the monitor includes a transfer assembly which transfers motion of the contact arm relative to the monitor base into rotational motion of the display.

17. The testing device of claim 16 wherein the transfer assembly includes an input component which rotates upon motion of the contact arm, a first transfer component which rotates upon rotation of the input component, a second transfer component which rotates upon rotation of the first transfer component, and an output component which rotates upon rotation of the second transfer component.

18. The testing device of claim 17 wherein the input component has an input component diameter which is larger than a first transfer component diameter of the first transfer component, the first transfer component diameter is smaller than a second transfer component diameter of the second transfer component and the second transfer component diameter is larger than an output component diameter of the output component.

19. A method for measuring the displacement of a patella in a leg of a patient, the method comprising the steps of:

applying a substantially lateral test force to the patella; and detecting lateral displacement of the patella with a monitor having a monitor base which is attached to the leg of the patient with a strap which substantially encircles the leg.

20. The method of claim 19 wherein the step of detecting lateral displacement of the patella includes contacting the leg proximate the patella with a contact arm which extends away from the monitor base.

21. The method of claim 19 wherein the step of applying a substantially lateral test force includes utilizing a displacer for applying the test force to the patella, the displacer including a pressure surface which is adapted for contacting the leg proximate the patella, a handle which is adapted for gripping by a human and a signaler which signals when the test force is applied to leg.

* * * * *